(12) United States Patent
Thorstensson

(10) Patent No.: US 8,196,809 B2
(45) Date of Patent: Jun. 12, 2012

(54) SYSTEM AND METHOD FOR ASSOCIATING AN ABSORBENT ARTICLE WITH A USER

(75) Inventor: Robert Thorstensson, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 385 days.

(21) Appl. No.: 12/593,661

(22) PCT Filed: Apr. 20, 2007

(86) PCT No.: PCT/SE2007/050258
§ 371 (c)(1), (2), (4) Date: Sep. 29, 2009

(87) PCT Pub. No.: WO2008/130298
PCT Pub. Date: Oct. 30, 2008

(65) Prior Publication Data
US 2010/0072271 A1    Mar. 25, 2010

(51) Int. Cl.
*G06F 17/00* (2006.01)
(52) U.S. Cl. ..................................... 235/375; 235/486
(58) Field of Classification Search .................. 235/375, 235/380, 382, 492, 493, 486, 487
See application file for complete search history.

(56) References Cited

U.S. PATENT DOCUMENTS

| | | | |
|---|---|---|---|
| 5,904,671 A * | 5/1999 | Navot et al. ................... | 604/361 |
| 6,774,800 B2 | 8/2004 | Friedman et al. | |
| 6,965,058 B1 | 11/2005 | Raidel et al. | |
| 7,250,547 B1 | 7/2007 | Hofmeister et al. | |
| 2002/0145525 A1 | 10/2002 | Friedman et al. | |
| 2004/0220538 A1 * | 11/2004 | Panopoulos ................... | 604/361 |
| 2004/0230172 A1 | 11/2004 | Shapira | |
| 2007/0204691 A1 | 9/2007 | Bogner et al. | |
| 2007/0273504 A1 * | 11/2007 | Tran .......................... | 340/539.12 |
| 2007/0276270 A1 * | 11/2007 | Tran .............................. | 600/508 |

(Continued)

FOREIGN PATENT DOCUMENTS
EP    0 911 000 A1    4/1999
(Continued)

OTHER PUBLICATIONS

International Search Report of Application PCT/SE2007/050258 dated Dec. 21, 2007.
Written Opinion of the International Searching Authority of Application PCT/SE2007/050258 dated Dec. 21, 2007.

(Continued)

*Primary Examiner* — Thien M Le
(74) *Attorney, Agent, or Firm* — Buchanan Ingersoll & Rooney PC

(57) ABSTRACT

A system for associating a particular absorbent article with the identity and/or the location of a user of the absorbent article, includes an absorbent article, and machine-readable information concerning the identity and/or the location of a user of the absorbent article. The system includes machine-readable information identifying the absorbent article and a reader to read the information identifying the absorbent article and the information concerning the identity and/or the location of a user of the absorbent article. The system also includes a memory that is arranged to store information identifying the absorbent article and information concerning the identity and/or the location of a user of the absorbent article in a form such that on retrieval of information from the memory, information concerning the absorbent article is automatically associated with information concerning the identity and/or location of a user of the absorbent article.

29 Claims, 7 Drawing Sheets

U.S. PATENT DOCUMENTS

| | | | |
|---|---|---|---|
| 2008/0294019 A1* | 11/2008 | Tran | 600/301 |
| 2009/0318779 A1* | 12/2009 | Tran | 600/301 |
| 2010/0072271 A1* | 3/2010 | Thorstensson | 235/375 |

FOREIGN PATENT DOCUMENTS

| | | |
|---|---|---|
| RU | 2213548 | 10/2003 |
| WO | WO 98/43684 | 10/1998 |
| WO | WO 2005/017683 A2 | 2/2005 |
| WO | WO 2006/119523 A1 | 11/2006 |

OTHER PUBLICATIONS

Craig A. Grimes et al., "Thin-Film Magnetoelastic Microsensors for Remote Query Biomedical Monitoring", Biomedical Microdevices, 1999, vol. 2, No. 1, pp. 51-60, 2000 Kluwer Academic Publishers, Boston. Manufactured in the Netherlands.

Office Action (Decision on Grant) dated May 31, 2011, issued in the corresponding Russian Patent Application No. 2009142847, and an English Translation thereof.

\* cited by examiner

SYSTEM AND METHOD FOR ASSOCIATING AN ABSORBENT ARTICLE WITH A USER

TECHNICAL FIELD

The present invention concerns a system and method for associating a particular absorbent article, such as a diaper, an incontinence garment, a sanitary napkin, a tampon-like product, a wound or sore dressing, a bed protector or a similar product with the identity and/or the location of a user of said absorbent article.

BACKGROUND OF THE INVENTION

There are many different types of absorbent articles for absorption, retention and isolation of body wastes such as urine, faeces and blood. Some of these known absorbent articles comprise a sensor for the detection of a soiling event, such as urination or defecation, on contact with a surface of the absorbent article or on absorption into the absorbent article. Such a sensor may, for example, be based on the detection of wetness or a biological or chemical substance in body waste, body exudates or the user's skin. When such a sensor detects a soiling event, a signal is generated, by means of which a user or caregiver, such as a parent or nursing personnel, may be made aware that a soiling event has occurred and that the absorbent article should be changed.

It is known to utilize a radiofrequency (RF) tag including an inductor-capacitor resonator as a sensor for the detection of a soiling event in an absorbent article. For example, this is described in U.S. Pat. No. 6,774,800. The RF tag may be utilized in an energy absorption mode or an energy radiation mode. In the energy absorption mode, the RF tag selectively absorbs energy from an excitation signal at its resonant frequency. This absorption produces a unique change in the excitation signal, which can be detected. When discharged fluid, such as urine, contacts the inductor-capacitor resonator of the RF tag, electrolytes in the discharged fluid create low resistance paths which detune the RF tag and thereby change its resonant frequency. A change of the resonant frequency may therefore be utilized to detect discharged fluid.

In the energy radiation mode the RF tag starts to oscillate at its resonant frequency in response to receiving an excitation signal. After termination of the excitation signal, energy stored in the RF tag causes the RF tag to continue oscillating at its resonant frequency. A response signal is thereby generated. In the presence of discharged fluid, the resonant frequency of the response signal is changed. A change of the resonant frequency of the response signal may therefore be utilized to detect discharged fluid.

In addition, it is also known to utilize a radio frequency identification (RFID) tag as a sensor for the detection of a soiling event in an absorbent article. An RFID tag that operates in the energy absorption mode absorbs energy from an excitation signal in one or more unique frequencies or unique bands of frequencies. When discharged fluid contacts said RFID tag, the fluid attenuates the excitation signal received by such an RFID tag whereby the selective absorption of energy by the RFID tag is reduced. Discharged fluid may therefore be detected.

U.S. Pat. No. 6,774,800 describes that in addition to the use of RFID tags as sensors for detection of a soiling event in absorbent articles, RFID tags that produce unique frequencies or bands of frequencies in either the energy absorption mode or energy radiation mode of operation can also be utilized for user identification. Each user of such an absorbent article in a location where there is a plurality of such users, such as a hospital or nursing home, may therefore be associated with particular frequencies or bands of frequencies produced by RFID tags that are different from the frequencies or bands of frequencies associated with all other users. Each user is then provided only with absorbent articles having RFID tags including the unique frequencies or bands of frequencies specifically assigned to him/her. However, such a system involves the risk that a specific user may be provided with the wrong absorbent article, i.e. an absorbent article having an RFID tag including frequencies or bands of frequencies that is assigned to another user. Such a mix-up may lead to erroneous data being stored in medical records and to an erroneous decision concerning when a particular absorbent article needs to be exchanged.

Another type of sensor that is utilized in some absorbent articles is the magneto-elastic sensor (which has been described by Grimes et al. in Biomedical Micro-devices, 2:51-60, 1999). A magneto-elastic sensor usually comprises a strip of magneto-elastic material. When excited by an external magnetic field, a magneto-elastic material stores magnetic energy in a magneto-elastic mode. When the magnetic field is switched off, the magneto-elastic material oscillates with a specific frequency called the magneto-acoustic resonant frequency. These oscillations give rise to a magnetic flux that varies in time, which can be read by a reader, such as a pick-up coil.

The reading of such a magneto-elastic sensor may be associated with the identity of a user of an absorbent article comprising such a sensor by providing the user with a machine readable identity tag and reading the sensor and the identity tag at the same time. Information concerning the identified user of the absorbent article may, in this way be collected and stored. Such a system avoids the risk of any mix-up occurring wherein a user is provided with an absorbent article that is intended for another user. When using such a system it must however be ensured that no other sensors are located in the vicinity of the user whose sensor reading is being taken since this may interfere with his/her reading and again lead to erroneous data being stored in medical records and to an erroneous decision of when a particular absorbent article has to be exchanged.

SUMMARY OF THE INVENTION

An object of the present invention is to provide an improved system associating a particular absorbent article with the identity and/or the location of a user of the absorbent article.

This object is achieved by a system comprising the features listed in claim 1, namely a system comprising an absorbent article and machine-readable information concerning the identity and/or the location of a user of the absorbent article. The system also comprises machine-readable information identifying the absorbent article, and a reader to read the information identifying the absorbent article and the information concerning the identity and/or the location of a user of the absorbent article. The system further comprises a memory that is arranged to store information identifying the absorbent article and information concerning the identity and/or the location of a user of the absorbent article in a form such that on retrieval of information from the memory, information concerning the absorbent article is automatically associated with information concerning the identity and/or location of a user of the absorbent article. Such a system does not require that a particular user is provided with a particular absorbent article. A user is instead provided with an absorbent article that is uniquely associated to him/her. The risk of providing a user with the wrong absorbent article is therefore eliminated, or at least reduced.

It should be noted that the expressions "reader" throughout this document is intended to include a reading unit that scans for information identifying the absorbent article and/or the information concerning the identity and/or the location of a user, or an interrogator unit that transmits and receives signals, such as a radio transmitter and receiver. Furthermore, the system comprises hardware and software components and does not include a human being that is able to carry out the same functions as the hardware and software components.

It should be noted that the reader may comprise one or more reading means. For example, if both the information identifying the absorbent article and the information concerning the identity and/or the location of a user are contained in RFID tags, a single reader may be arranged to read information identifying the absorbent article and the information concerning the identity and/or the location of a user. Alternatively, if the information identifying the absorbent article is contained in an RFID tag and the information concerning the identity and/or the location of a user is contained in a bar code for example, the reader may comprise reading means to read information identifying the absorbent article and separate reading means to read the information concerning the identity and/or the location of a user.

According to an embodiment of the invention the absorbent article comprises a machine-readable sensor that is arranged to determine and indicate the status of at least a region of the absorbent article, whereby the system comprises means to associate the status indication from the machine-readable sensor with information concerning the identity and/or location of a user of the absorbent article or information identifying the absorbent article. When the sensor detects that a soiling event has taken place, a detectable response is generated, which may be detected by a reader. A sensor may for example operate at a particular resonant frequency. Information concerning the resonant frequency of the sensor then constitutes at least part of the information identifying the absorbent article so that status indications from that sensor may be correlated with a particular absorbent article and consequently with a particular user.

Such a system allows a caregiver to determine whether or not an absorbent article needs to be changed, without the need for close inspection or removal of the absorbent article. Furthermore, the risk of a sensor reading leading to erroneous data being stored in medical records or of an erroneous decision concerning when a particular absorbent article has to be exchanged is eliminated, or at least reduced.

According to a further embodiment of the invention the sensor is arranged to communicate via radio frequency communication. The sensor may, for example, comprise an RF tag or may be realized as BlueTooth® or wireless local area network (WLAN) communication means, or radio frequency identification (RFID) communication means, such as an RFID tag. In embodiments where the sensor is an RFID tag, the RFID tag may also contain information identifying the absorbent article. Once information identifying an absorbent article and information concerning the identity and/or location of a user has been stored in the memory, only readings from the sensor which concern the status of at least a region of an absorbent article need to be taken.

According to an embodiment of the invention the sensor is integrally formed with the absorbent article, i.e. the sensor is an integral part of the absorbent article and cannot be removed or disassembled without destroying either the absorbent article or the sensor or both. Such a sensor may for example comprise at least one electrical circuit that is fabricated from an electrically active material which has been printed onto one or more components of the absorbent article.

According to an embodiment of the invention the sensor is a wetness-detecting sensor, i.e. a sensor that detects moisture, liquid or humidity.

According to another embodiment of the invention the system comprises means to indicate, to a parent or to nursing personnel for example, that the status of the absorbent article has changed, by means of an optic, acoustic or tangible alarm signal for example.

According to a further embodiment of the invention the information concerning the identity and/or location of a user is arranged to be located in the vicinity of a user of the absorbent article, such as in the user's room, on the user's bed or the user's medical records, and/or to be attached to a user of the absorbent article, independently of the absorbent article, by means of a wristband, for example. In cases where a user is mobile, the information concerning the location of the user may be determined using a global positioning (GPS) system, whereby information concerning the location of a user is contained in a GPS receiver.

According to an embodiment of the invention the information concerning the identity and/or location of a user and/or the information identifying the absorbent article is separately contained in an optically readable code such as a bar code, a Radio Frequency Identification (RFID) tag, biometric information, a magnetic strip, optical characters or a smart card. The information may be communicated using radio frequency communication and the system may, for example, comprise an RF tag or may be realized as BlueTooth® or wireless local area network (WLAN) communication means, or radio-frequency identification (RFID) communication means.

An RFID tag typically comprises a device, such as a microchip, that may be used to store information identifying an absorbent article, such as a unique serial number or information concerning the identity/location of a user, such as a patient's name or a patient's room number. A reader communicates with the RFID tag through radio waves. The microchip is attached to an antenna that receives signals from, and sends signals to the reader. Furthermore, an RFID tag can be an active tag, a passive tag or a semi-passive tag. Active tags include a power source that powers the microchip's circuitry and transmits a signal to the interrogator. Passive tags do not include a power source. Passive tags draw the power required for the circuitry and the transmission of information from the electromagnetic field generated by the reader. Semi-passive tags are similar to active tags; however the power source is used to run the microchip's circuitry, but not to communicate with the reader.

According to a further embodiment of the invention the system includes data storage means arranged to record data concerning a user of the absorbent article. For example, stored data may include information on how often a user's absorbent article has been changed over a period of time and how often soiling events occur. Such information may be utilized to determine the type of absorbent article that should be utilized for a specific user, or if different absorbent articles needed during the day and during the night, or to make predictions for future consumption of absorbent articles.

According to an embodiment of the invention the system comprises a plurality of such absorbent articles. The status of all of the plurality of absorbent articles may thus be determined in a single sensor reading operation.

The present invention also concerns a method for associating information identifying an absorbent article with information concerning the identity and/or the location of a user of the absorbent article. The method comprises the steps of a) obtaining information identifying the absorbent article, b) obtaining information concerning the identification and/or location of a user of the absorbent article, simultaneously or in sequence although not necessarily in that order, and c) storing the information identifying the absorbent article and the information concerning the identification and/or location of a user of the absorbent article in a memory in a form such that on retrieval of information from the memory, information concerning the absorbent article is automatically associated with information concerning the identity and/or location of a user of the absorbent article.

According to an embodiment of the invention steps a) and b) of the method are carried out when an absorbent article is put on a user.

According to another embodiment of the invention the method comprises the step of providing the absorbent article with a machine-readable sensor that is arranged to determine and indicate the status of at least a region of the absorbent article and associating the status indication from the machine-readable sensor with information concerning the identity and/or location of a user of the absorbent article or information identifying the absorbent article.

According to a further embodiment of the invention the sensor is arranged to communicate via radio frequency communication.

According to an embodiment of the invention the sensor is integrally formed with the absorbent article.

According to another embodiment of the invention the sensor is a wetness detecting sensor.

According to an embodiment of the invention the method comprises the step of indicating, to a parent or to nursing personnel for example, that the status of the absorbent article has changed, by means of an optical, acoustic or tangible alarm signal for example.

According to another embodiment of the invention the method comprises the step of locating the information concerning the identity and/or location of a user in the vicinity of a user of the absorbent article or attaching the information to a user of the absorbent article, independently of the absorbent article, by means of a wristband for example.

According to a further embodiment of the invention the information concerning the identity and/or location of a user and/or the information identifying the absorbent article is separately contained in an optically readable code such as a bar code, a Radio Frequency Identification (RFID) tag, biometric information, a magnetic strip, optical characters or a smart card.

According to another embodiment of the invention the method comprises the step of recording data concerning a user of the absorbent article.

According to a further embodiment of the invention the method comprises the step of associating information identifying a plurality of absorbent articles with information concerning the identity and/or the location of users of the plurality of absorbent articles. Such a method may be used to monitor the status of a plurality of absorbent articles.

The present invention also concerns a computer program product that comprises a computer program containing computer program code means arranged to cause a computer or a processor to execute the steps of a method according to any of the embodiments of the invention, stored on a computer-readable medium or a carrier wave.

It should be noted that the drawings have not been drawn to scale and that the dimensions of certain features have been exaggerated for the sake of clarity.

DETAILED DESCRIPTION OF EMBODIMENTS OF THE INVENTION

Figure 1:
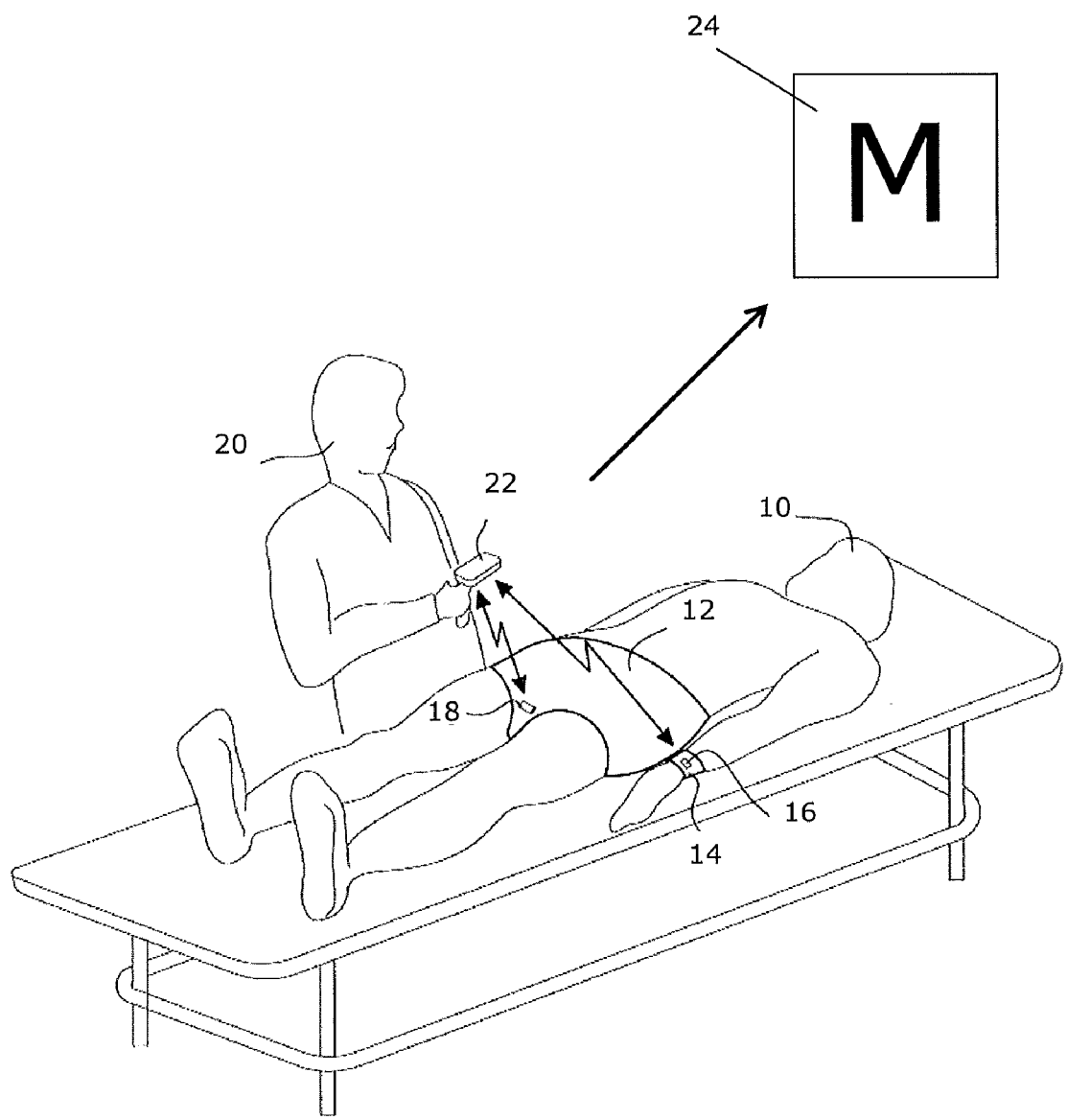
FIG. 1 shows a system according to an embodiment of the invention.

FIG. 1 shows a patient 10 wearing an absorbent article 12. The patient 10 may be an incontinent adult, an infant or an animal. The patient 10 is wearing a wristband 14 comprising machine-readable information 16 concerning his identity in the form of a bar code. The absorbent article 12 comprises machine-readable information 18 identifying the absorbent article. A nurse 20 equipped with a portable reader 22 reads the information 18 identifying the absorbent article 12 and the information 16 concerning the identity of the patient 10. The information is transmitted to a remote memory 24, via an RF modem for example, where it is stored in a form such that on retrieval of information from the memory 24, information concerning the absorbent article 12 is automatically associated with information 16 concerning the identity of the patient 10.

Figure 2:
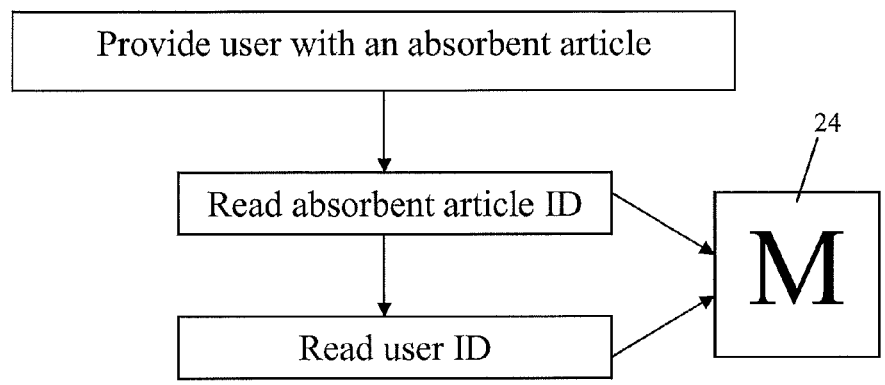
FIG. 2 is a flow chart illustrating a method according to an embodiment of the invention.

FIG. 2 is a flow chart showing the steps of a method for associating information identifying an absorbent article with information concerning the identity and/or the location of a user of the absorbent article. The method comprises the steps of providing a user with an absorbent article, obtaining information identifying the absorbent article, obtaining information concerning the identification and/or location of a user of the absorbent article in any order, and storing the information in a memory 24 in a form such that on retrieval of information from the memory 24, information concerning the absorbent article is automatically associated with information concerning the identity and/or location of a user of the absorbent article.

Figure 3:
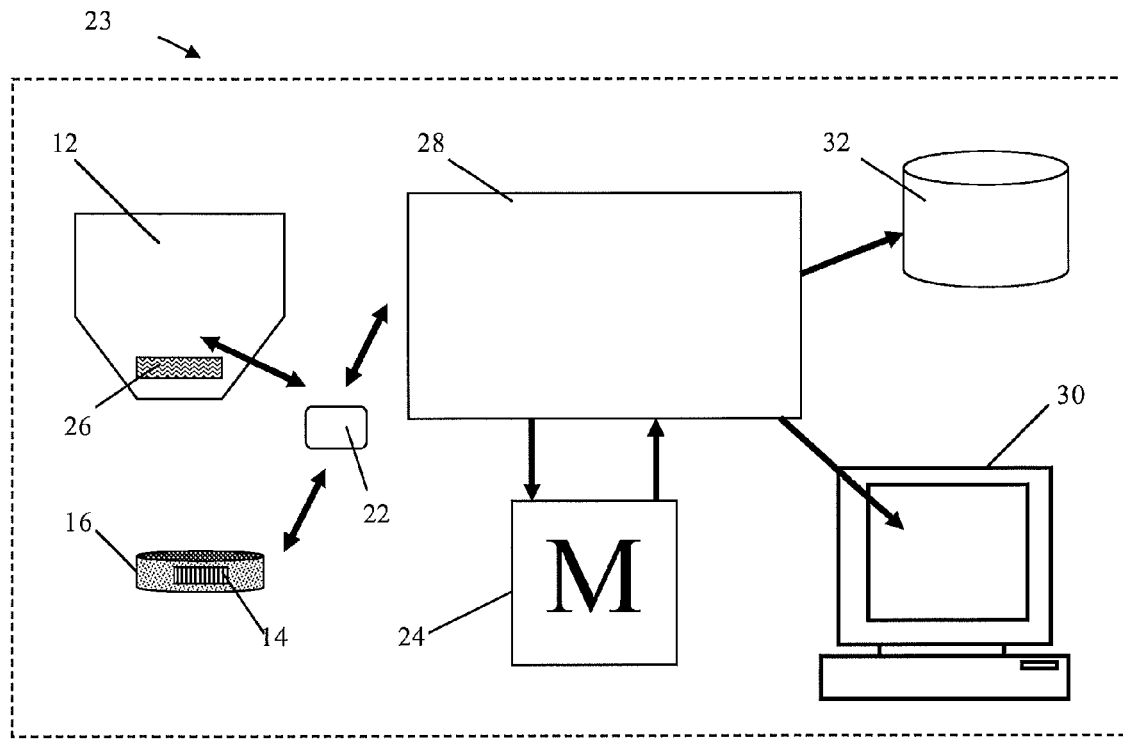
FIG. 3 shows a system according to another embodiment of the invention.

FIG. 3 shows a system 23 according to an embodiment of the invention. The system 23 comprises an absorbent article 12 comprising an integrated wetness sensor 26, such as an RFID tag, that contains information identifying the absorbent article 12. When the absorbent article 12 is put on a user (not shown) the information identifying the absorbent article 12 is read using a reader 22 together with information concerning the identity or location of a user and this information is transmitted to a memory 24 where it is stored. The status in the crotch portion of the absorbent article 12 is subsequently detected and a signal is transmitted to a processing unit 28. On receiving the status indicating signal from the sensor 26, the processing unit 28 retrieves information identifying the absorbent article 12 which comprises a sensor 26 that is capable of sending such a signal. This information is automatically associated with information concerning the identity and/or location of the user wearing that particular absorbent article 12.

A caregiver may then be informed that that particular user's absorbent article needs to be changed, by means of a signal sent to his/her personal computer 30 and/or pager for example. Once the caregiver has changed that user's absorbent article, he/she obtains information identifying the fresh absorbent article and information concerning the identity and/or location of the user. The obtained, updated information is then stored in the memory 24. Information concerning the status of a user's absorbent articles may also be sent to a data storage means 32, where data concerning that user's behaviour is logged for future comparisons with other data for that specific user.

Figure 4:
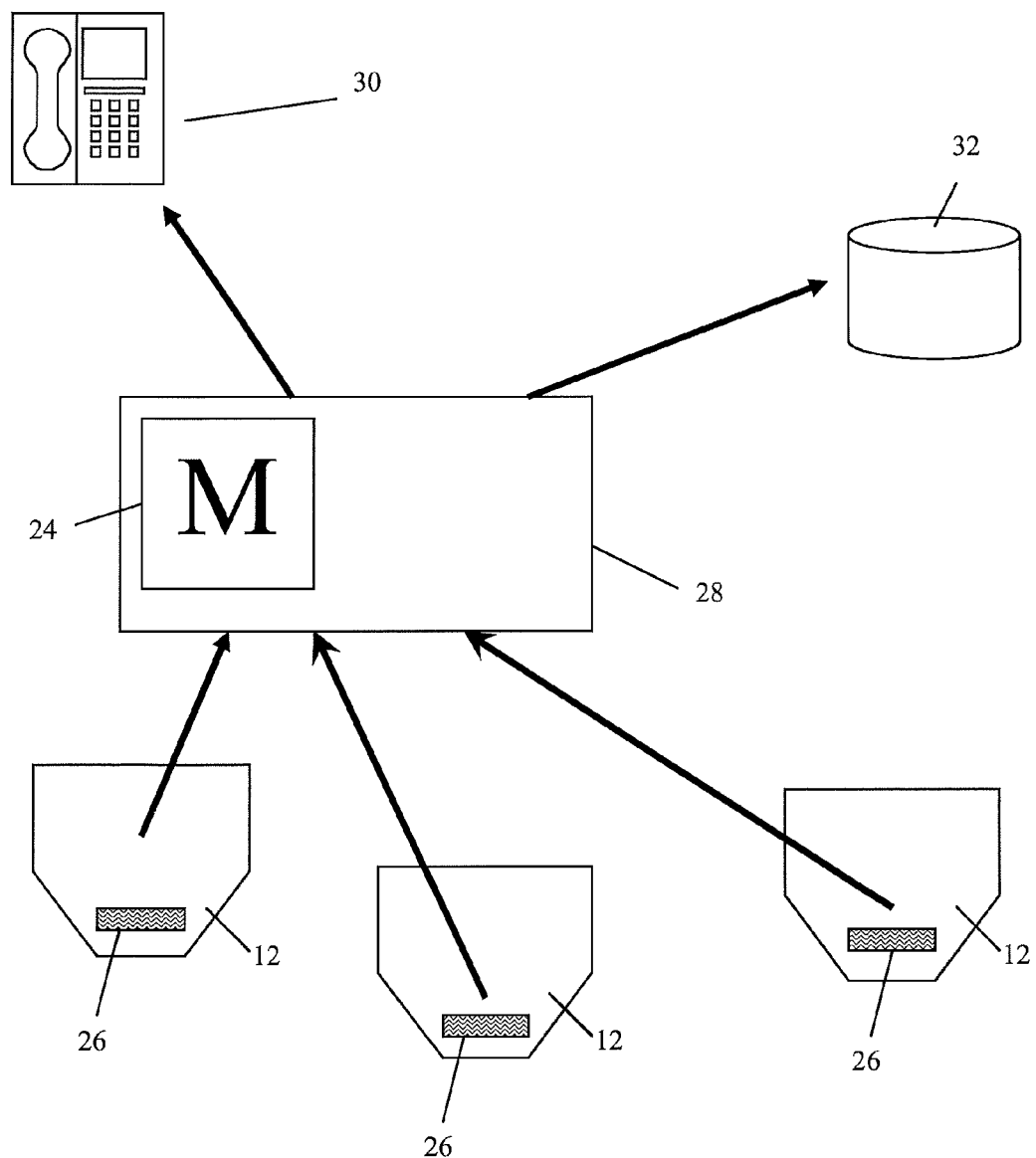
FIG. 4 shows a system comprising a plurality of absorbent articles according to an embodiment of the invention.

FIG. 4 shows a system that monitors the status of a plurality of absorbent articles 12 comprising sensors 26 (all of which are exemplified as diapers although the system may monitor any number of different types of absorbent article). Each sensor 26 comprises an RFID tag that contains information, such as an article number, identifying the absorbent article and that communicates the status of the absorbent article 12 in the crotch region of the absorbent article 12, i.e. whether it is wet or dry. All of the sensors 26 are scanned periodically. If the status of any of the sensors changes between two consecutive scans, the absorbent article 12 containing the sensor 26 whose status has changed is identified, whereby the status of that absorbent article 12 is automatically associated with information concerning the identification and/or location of the user wearing that particular absorbent article 12. This information is transmitted to a caregiver monitoring that user, by means of a signal to that person's fixed or mobile telephone 30, or personal digital assistant for example and is also logged in data storage means 32.

Figure 5:
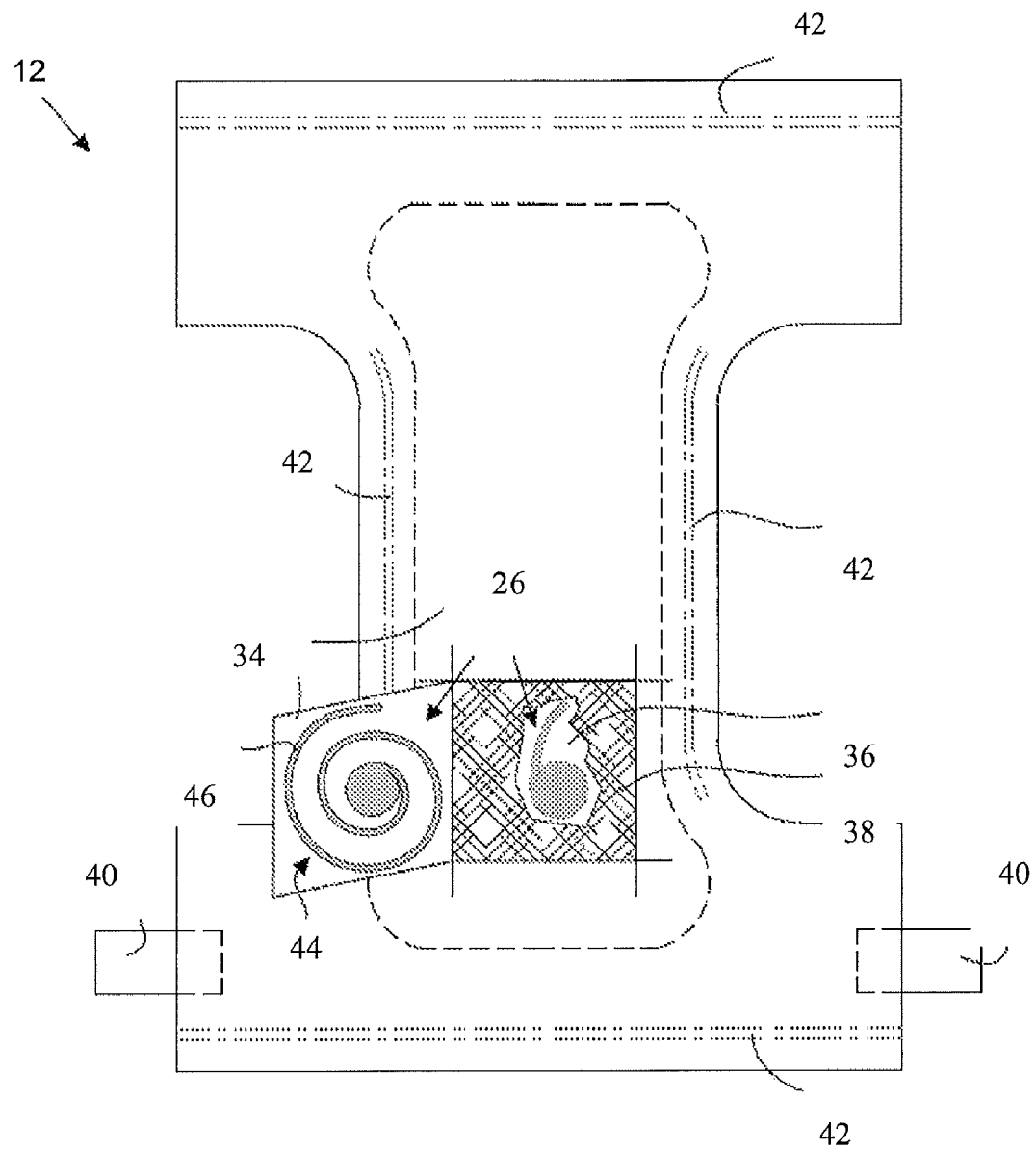
FIG. 5 shows an absorbent article for use in a system according to an embodiment of the invention.

FIG. 5 shows an absorbent article 12 that may be used in a system according to an embodiment of the invention. The absorbent article 12 comprises a liquid-permeable topsheet 34, a liquid-impermeable backsheet 36 and an absorbent core 38 located therebetween.

The liquid-permeable topsheet 34 optionally consists of a nonwoven material, e.g., a spunbond material of continuous filaments, a meltblown material, a bonded carded fibrous web or a perforated plastic film. Different types of laminates, e.g. laminates of non-woven material and plastic film may optionally also be used. Materials which are suitable for the liquid-permeable topsheet 34 should be soft and non-irritating to the skin. Furthermore, the topsheet 34 can be different in different regions of the article 12.

The liquid-impermeable backsheet 36 may consist of a plastic film, a nonwoven material treated with a liquid impervious material or a hydrophobic nonwoven material which resists liquid penetration. Other types of liquid-barrier-materials may of course also be used as the liquid-impermeable backsheet 36, such as e.g. closed-cell plastic foams, various liquid-barrier laminates etc. It is preferable that the liquid-impermeable backsheet 36 is permeable to air and vapour.

The topsheet 34 and the backsheet 36 have a somewhat greater extension in the plane than the absorbent core 38 and extend outside the edges thereof. The topsheet 34 and the backsheet 36 are connected to each other within the projecting regions thereof, e.g., by gluing or welding by heat or ultrasound.

The absorbent core 38 can be of any conventional kind. Examples of commonly-occurring absorbent materials are cellulosic fluff pulp, tissue layers, highly absorbent polymers (so-called "super-absorbents"), absorbent foam materials, absorbent non-wovens and the like. It is common to combine cellulosic fluff pulp with super-absorbents in an absorbent body. It is also common to have absorbent bodies comprising layers of different material with different properties with respect to liquid acquisition capacity, liquid distribution capacity and storage capacity. The thin absorbent bodies which are common in incontinence guards often comprise a compressed mixed or layered structure of cellulosic fluff pulp and super-absorbent.

Absorbent articles such as diapers usually require some sort of fastening means 40 which hold the absorbent article 12 closed. Suitable fastening means 40 may be mechanical fasteners such as hook-and-loop type fasteners, adhesives such as pressure-sensitive adhesives or a combination of mechanical and adhesive fasteners.

If the absorbent article 12 is a belt diaper, it will comprise belt regions, such that the belt regions comprise a sole component of the waist region of the diaper. The belt regions are attached or fastened to the front or the rear region of the article, and fasten to each other around the waist of the user. The article is then passed between the legs of the user and fastened to the belt regions via the other of the front or rear region. Fastening means 40 as described above are present on the belt regions and on the front/rear region so that the absorbent article 12 can be firmly closed. Application of the absorbent article 12 implemented in this way allows a user to easily apply the belt diaper themselves, and even allows a diaper to be changed while the user is standing up.

Elastic elements 42 may be present in the absorbent article 12, for example at the leg or waist openings. The nature and location of such elastic elements 42 are known to the skilled person and need not be discussed further here.

The absorbent article 12 comprises at least one wetness detecting sensor 26. This sensor 26 typically has a first electrical characteristic before the absorbent article 12 is soiled and a second electrical characteristic after a soiling event has occurred.

Electrically active materials 46 may be printed on the absorbent article 12. The term "electrically active" is used in the present context to mean materials which can conduct electrical charge and thus be used to fabricate electrical circuits or components thereof. The electrically active materials 46 are stable in liquid or solution form (i.e. can be solution-processed) and can be applied to a surface (in this case, a component of the absorbent article 12) in a desired pattern or form, which pattern or form is then retained after the material dries or cools. The electrically active materials 46 should also have mechanical properties which make them tolerant to flexing and tension which might be present in the absorbent article 12. They should also be stable to the environment in which they are to be used (i.e. stable to humidity, sunlight, oxygen etc.). Printing can be carried out using standard techniques known in the art, such as laser printing, inkjet printing, thermal printing, screen printing, offset printing, relief print and rotogravure. An absorbent article comprising a printed circuit is does not significantly increase the size or stiffness of the absorbent article, is readily disposable and quite easy to manufacture using a rapid assembly-line manufacturing method.

Conductive polymers are one class of electrically active materials 46 which are printable. Such polymers generally have structures in which the electrons are heavily delocalised, e.g. through π-bonds (double or triple bonds), aromatic systems or electron lone pairs which are included in the polymer chain. The electrons are therefore free to move along the polymer structure. The extent of delocalisation determines the degree of conductivity—polymers which have poorly delocalised electrons will be less conducting than those having continuous delocalisation across the entire polymer structure. Examples of conducting polymers are polyphenylenevinylene (PPV), polyaniline (PANI) and polypyrrole (PPy). The structures of these polymers are given below.

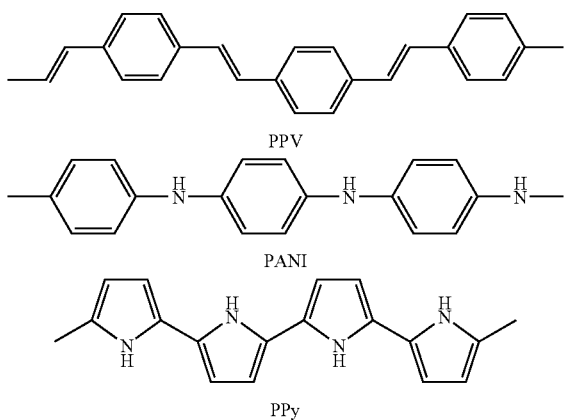

The electrical, mechanical and chemical properties of such polymers can be adjusted as desired, by, for example, cross-linking or substitution of the polymer, or combining them with other materials before printing. In many cases, these polymers need to be protected from air and humidity by laying a printed barrier film over the polymers, or by depositing the polymers simultaneously with a barrier matrix.

Another class of printable electrically active materials 46 are particle suspensions. These materials comprise small particles of an electrically-conducting material (e.g. a metal such as silver or copper, or a non-metal such as graphite) which are suspended in an organic solvent or carrier. The particles provide the material with the desired conductivity, while the organic solvent or carrier provides the required physical properties (e.g. plasticity, coefficient of thermal expansion, ease of application, viscosity and fracture toughness). The organic solvent or carrier may also contribute to the electrical properties of the electrically active material. The organic solvent may evaporate after printing, in which case, the particles remain on the printed surface. Alternatively, the organic carrier hardens after printing, so that the particles are trapped within the carrier. Examples of the latter embodiment are epoxy resins. Such particle suspensions are commercially available from DuPont electronics or TÄBY Sweden. The printable electrically active materials 46 may comprise a mixture of the above-described particle suspensions and conductive polymers.

It is possible for different electrically active materials 46 to be printed in different regions or components of an absorbent article 12, depending on the type of electrical circuit which is required. By repeatedly printing electrically active materials 46 (optionally having different electrical properties) on the same region or component, it is possible to build up layers of electrically active material on top of each other. Alternatively, electrical components can be fabricated with intervening layers of the components of the absorbent article, so that a sandwich-type structure is created. This can be seen in the cut-away view in FIG. 5. The components of the absorbent article 12 may be selected or treated to be permeable or resistant to the electrically active material. All of these approaches allow complex electrical circuits to be manufactured.

The wetness detecting sensor 26 comprises an electrical circuit 44, which is integrally formed into the absorbent article 12, the at least one electrical circuit 44 being fabricated from an electrically active material 46 which has been printed onto one or more components of the absorbent article 12.

Electrical circuits fall into two general classes—active circuits, which comprise a power source as a component of the circuit, and passive circuits, which do not comprise a power source as one of their components, but act in response to an externally-applied power source.

In certain circumstances, the electrically active material 46 can penetrate into the components of the absorbent article 12.

Figure 6:
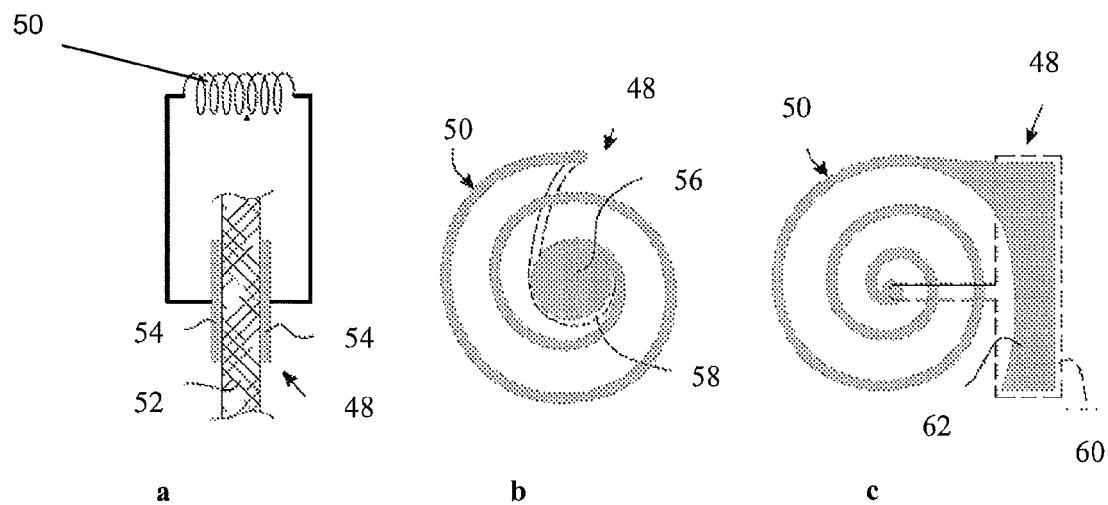
FIGS. 6a-c show an electrical circuit that may be printed on absorbent article for use in a system according to an embodiment of the invention, FIGS. 7a & b show a second electrical circuit that may be printed on absorbent article for use in a system according to an embodiment of the invention, FIGS. 8a & b show a third electrical circuit that may be printed on absorbent article for use in a system according to an embodiment of the invention.

FIG. 6a shows a circuit diagram of a tuned circuit (also called an RLC circuit) which consists of a capacitor 48 and an inductor 50. There will naturally be a certain amount of resistance from the circuit; alternatively, resistors may be included in parallel or in series with the capacitor 48 and the inductor 50.

The capacitance C of a capacitor may be expressed mathematically as:

$$C = \frac{A\varepsilon_0\varepsilon_r}{d}$$

wherein A is the area of the capacitor plates (in m²), d is the distance between the plates (in m), $\varepsilon_0$ is the permittivity of free space (ca. $8.8542\times10^{-12}$ F/m) while $\varepsilon_r$ is the relative permittivity of a dielectric included between the capacitor plates, for example the capacitor 48 includes a layer 52 of dielectric between its plates 54. Cellulose in paper and cotton products has a relative permittivity of approximately 6.5. Non-impregnated dry tissue (kraft) paper has a relative permittivity of around 2.1. Polymers such as polyethylene and polypropylene have relative permittivities in a range of substantially 2.2-2.5. (Reference: Kaye & Laby, *Tables of Physical and Chemical Constants*, 15$^{th}$ ed. 1986)

At a simple level, the inductance L of an inductor is expressed mathematically as:

$$L = \frac{N^2 A \mu_0 \mu_r}{l}$$

wherein $\mu_0$ is the permeability of free space ($4\pi\times10^{-7}$ Henries per metre), $\mu_r$ is the relative permeability of the core (dimensionless), N is the number of turns in the inductor, A is the cross sectional area of the inductor in square metres and l is the length in metres.

The resonance frequency $f_0$ of a tuned circuit can be calculated from the values of L and C using:

$$f_0 = \frac{1}{2\pi\sqrt{LC}}$$

Hence, upon application of an external RF field, a tuned circuit such as that illustrated in FIG. 6a resonates at a natural resonant frequency, which can be adjusted through choice of capacitor and inductor variables listed above.

A change in the moisture-content of the absorbent article 12 influences the resonant frequency $f_0$ of the electrical circuit 44. There are a number of ways in which this might be achieved.

Firstly, the moisture-content of the absorbent article 12 may influence the capacitance of the capacitor 48. For example, a water-swellable material may be present in the dielectric layer 52 between the plates 54 of the capacitor 48, so that, upon wetting, the distance d increases, and the capacitance decreases. Alternatively, liquid-absorbent material (such as superabsorbent polymer (SAP), cellulose or any other liquid-absorbent material) may be present in the dielectric layer 52 between the plates 54 of the capacitor 48. The absorption of liquid into the liquid-absorbent material has the effect of increasing the relative permittivity ($\in_r$) of the liquid-absorbent material (as water has a high relative permittivity), thus increasing the capacitance of the capacitor 48.

As a further alternative, a water-soluble substance such as an inorganic salt may be present in the dielectric layer 52 between the plates 54 of the capacitor 48. The water-soluble substance dissolves upon contact with liquid and thus the capacitance of the capacitor 48 will change, and the resonant frequency $f_0$ of the circuit will alter.

As a further alternative, a change in resistance of the circuit will change the resonant frequency $f_0$ of the circuit. A change in the moisture-content of the absorbent article 12 influences the resistance of the electrical circuit 44. This may be, for example, achieved by using conductive polymer materials protected by a water-soluble barrier film (e.g. an epoxy material). Upon wetting, the film dissolves and water, salts and urea will react with the conductive polymer material, changing the resistance of the circuit and thereby the resonant frequency $f_0$.

When printed onto a component of the absorbent article 12, such as a paper sheet or a plastic film, the circuit illustrated diagrammatically in FIG. 6a may be in the form shown in FIG. 6b. FIG. 6b shows an inductor 50 which comprises a flat spiral printed in electrically active material 46 on a component of the absorbent article 12. The spiral typically has between 5-20 turns. The spiral has a first central area 56. A corresponding second central area 58 is printed on the opposite face of the component of the absorbent article 12—together these two central areas 56, 58 constitute the plates of the capacitor 54 which are separated by the component of the absorbent article 12. The circuit is completed by electrically active material which connects the second central area 58 to the outer end of the spiral, through the component of the absorbent article 12.

An alternative form for printing the circuit illustrated diagrammatically in FIG. 6a is shown in FIG. 6c. FIG. 6c illustrates the inductor 50 which comprises a flat spiral form as in FIG. 6b. The capacitor 48 is formed by first 60 and second 62 areas lying on opposite faces of the component of the absorbent article 12, outside the area comprised by the spiral. Together, these first 60 and second 62 areas constitute the plates of the capacitor 54.

Figure 7:
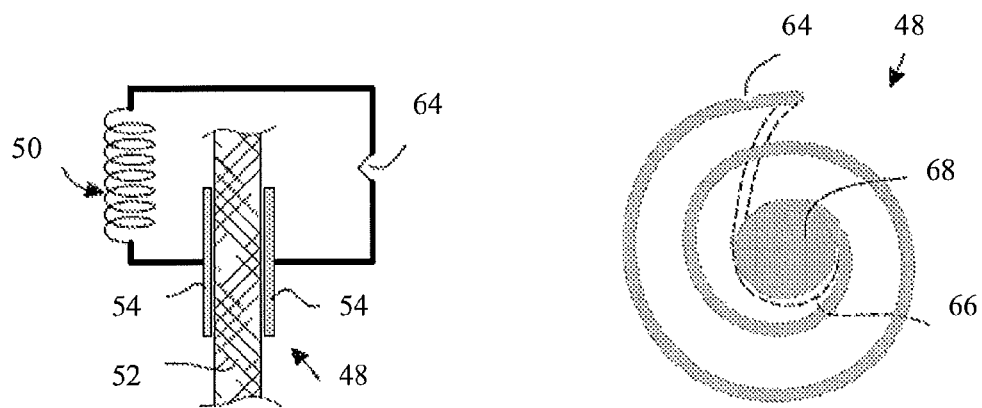

An alternative way in which the moisture-content of the absorbent article 12 can influence the resonant frequency $f_0$ of the electrical circuit 44 is through destruction, namely disablement, of the electrical circuit 44. In other words, a change in the moisture content of the absorbent article 12 destroys the resonant frequency $f_0$ of the electrical circuit 44. This may be achieved through an electrical circuit as illustrated in FIG. 7a.

Such a circuit comprises a weak point 64, which for instance comprises water-soluble electrically active material, or electrically active material which is printed on a water-soluble component. An absorbent article comprising such the electrical circuit illustrated in FIG. 7a will resonate at its resonant frequency upon application of an external RF field. Upon contact with a liquid, however, the electrical circuit 44 is physically broken and by virtue of the weak point 64 becoming a high-resistance or substantially open-circuit, the electrical circuit 44 will not then resonate upon application of an external RF field.

FIG. 7b shows how the electrical circuit 44 illustrated diagrammatically in FIG. 7a may be printed. In its printed form, the electrical circuit 44 has essentially the same form as that shown in FIG. 6b, with an inductor 50 which comprises a flat spiral and two central areas 66, 68 which constitute the plates 54 of the capacitor 48. The circuit shown in FIG. 7b includes a weak point 64 which is broken upon contact with a liquid.

In a further embodiment, the electrical circuit 44 may comprise a sensor 70 connected in parallel or in series with the capacitor 48 and the inductor 50. A change in the moisture-content of the absorbent article 12 influences the conductance of a current across the sensor 70. A circuit diagram which illustrates the use of a sensor 50 is shown in FIG. 8a.

Printed sensors 70 may take a number of forms. One possibility is to print the sensor 70 in a sandwich structure similar to those described for capacitors 48 above. This construction requires two layers of electrically active material 46 separated by a dielectric material. Alternatively, the sensor may have an interdigitated construction, in which electrically active material 46 is printed as a pair of "fork" shapes in which the prongs of the forks are interleaved, but without electrical contact between the prongs. This layout is advantageous, as it can be printed in one layer, making it less expensive to print than multiple layers. Hence, in one embodiment of the present invention, the wetness detecting sensor 26 is printed on a component of the absorbent article 12 which lies adjacent to the inner surface of a backsheet 36 of the absorbent article 12.

The principles involved in the sensor 70 are similar to those involved in the capacitor 48. Upon contact with liquid, the permittivity of the sensor 70 changes. This may be achieved by the physical dimensions or the relative permittivity of the sensor 70 changing upon contact with liquid. As a result, the resonant frequency $f_0$ of the tuned circuit changes.

Figure 9:
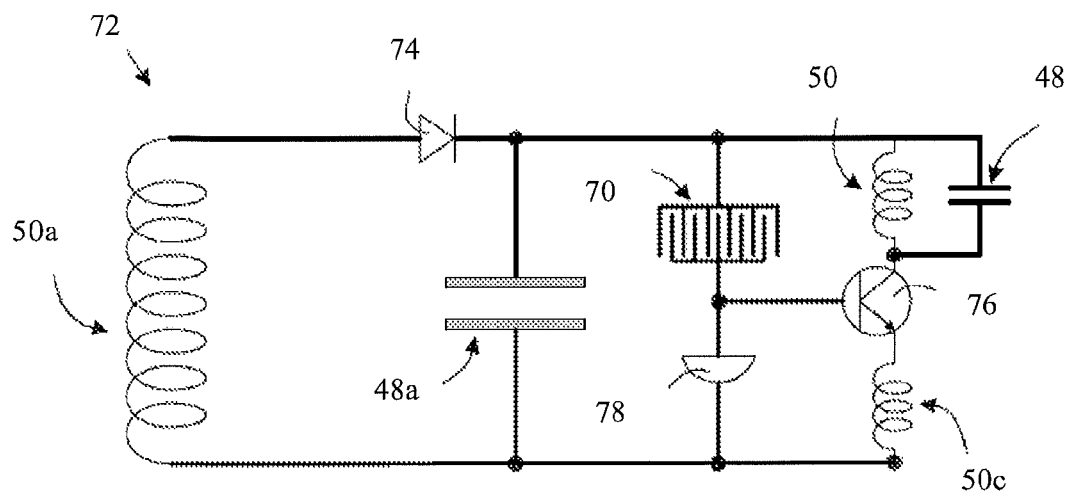
FIGS. 9 & 10 show a fourth electrical circuit that may be printed on absorbent article for use in a system according to an embodiment of the invention.

FIG. 9 shows a circuit diagram of a more advanced electrical circuit, indicated generally by 72, which may make up the wetness detecting sensor 26. A major circuit comprises a first inductor 50a, a first capacitor 48a and a sensor 70 connected in parallel, with a diode 74 located in series with the first inductor 50a. The sensor 70 is connected in parallel via a transistor 76 with a minor circuit which is itself a tuned circuit comprising a second inductor 50b and a second capacitor 48b. The transistor 76 is further connected via a high resistance bias resistor 78 and a third inductor 50c.

Operation of the more advanced electrical circuit 72 will now be described. In operation, the circuit 72 is subjected to an alternating magnetic field at a first frequency $f_1$: the first frequency is beneficially in a range of 10 kHz to 100 kHz. The first inductor 50a is arranged to include sufficient turns and be of sufficient area A so that a signal induced across the first inductor 50a has an amplitude of the order of a few volts. The diode 74 is operable to rectify the signal so as to generate a working supply potential in operation across the first capacitor 48a.

When the sensor 70 is dry (i.e. a soiling event has not yet occurred), the transistor 76 of NPN type or MOS type is biased into a non-conducting state by virtue of the bias resistor 78; in such a non-conducting state, the transistor 76 is hindered from oscillating.

When a soiling event occurs, the sensor 70 becomes conductive, causing the transistor 76 to be biased into an active part of its characteristic: in consequence, positive feedback occurs between the second and third inductors 50b, 50c causing the transistor to oscillate at a frequency $f_2$ defined by the second inductor 50b and the second capacitor 48b. Optionally, the second frequency $f_2$ is substantially at least an order of magnitude greater than the frequency $f_1$ of exciting magnetic field applied.

Figure 8:
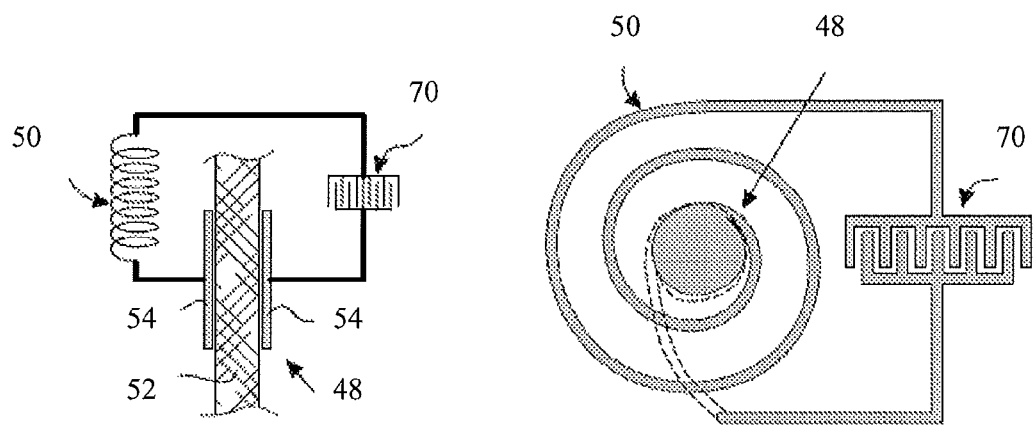
Figure 10:
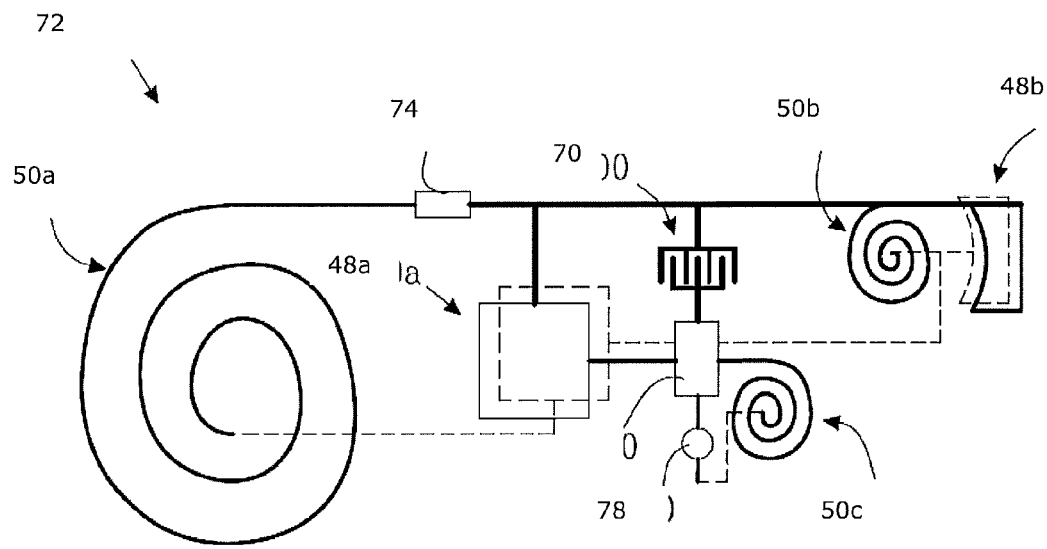

FIG. 10 illustrates how the electrical circuit 500 of FIG. 4 might be printed on an absorbent article 12. The first inductor 50a comprises a relatively large number of coils (e.g. 50-500), and may be printed together with the first capacitor 48a in the same way as the circuits illustrated in FIGS. 5-8. The sensor 70 may be printed in the same way as illustrated in FIG. 8. Diode 74 can be printed laying down multiple layers of electrically active material with selected electrical properties so as to build the required p-n junctions. Similarly, layers of electrically active material with different electrical properties can be used to build up transistor 76, either in MOS or bipolar implementation. Recently all-printed transistor devices with mobilities as high as 0.1-0.2 $cm^2$/V-s and on-off ratios as high as $10^4$ were reported (University of California, Berkeley). First, a gate electrode is printed onto a substrate using gold nano-crystals. This is followed by low-temperature annealing, and then polymer dielectric is deposited via inkjet printing. Source/drain contacts are then printed, again using gold nano-crystals.

The second and third inductors 50c, 50c comprise fewer coils than the first inductor (e.g. 5-20 coils) and may be printed together with the second capacitor 48b in the same way as the circuits illustrated in FIGS. 5-8. It is desirable that the first inductor 50a is distant from the second and third inductors 50b, 50c, so that coupling between the first inductor 50a and the second and third inductors 50b, 50c is minimised. For instance, the first inductor 50a could be located on the rear of the absorbent article 12, while the second and third inductors 50b, 50c are located on the front of the absorbent article 12. Suitably, the sensor 70 is printed in the crotch region of the absorbent article 12, which is the area in which wetting is easiest to detect. High frequency radiation at the frequency $f_2$ can be detected in an external detector device (e.g. transponder unit 28) which is selectively responsive to emitted radiation from the article 12 at the frequency $f_2$.

As an alternative to the above-described passive wetness detecting means 26, the wetness detecting means 26 may be active, i.e. it comprises a power source. Although such active wetness detecting means 26 are more complicated, they can provide a much wider functionality than passive wetness detecting means. A printed electrical circuit 43 can be divided into five major parts. These are printed batteries, printed antennae, printed memory circuits, printed logic circuits and printed sensors. The most essential components are printed batteries, printed antennae and printed sensors.

Printed batteries comprise an electrolyte sandwiched between two electrodes. In printed batteries, the electrolyte is usually in the form of a gel which is sealed so as to avoid leakage. Suitable electrolytes are carbon-zinc electrolytes or zinc-manganese dioxide. One possible structure for a printed battery is alternating layers of zinc and manganese dioxide-based cathode and anode layers. Printed batteries may have a thickness which is generally between 0.5 and 1 mm, and, if circular in form, a diameter which is between 25 and 50 mm. Typical output voltages are 1.5 V; the same as many conventional batteries. They are manufactured by standardised printing, drying and laminating equipment and processes. Printed batteries are commercially available from e.g. PowerPaper Ltd. of Israel or Thin Battery Technology (TBT) Inc of the USA. The battery itself may function as a sensor. Printed batteries can be made in such a way that they are inactive until contacted by a liquid. Upon activation (wetting), the battery sends a current to a circuit including one or more antennae. This generates an RF signal. Such batteries remove the need for a separate sensor, and are storage-stable.

Antennae are available as printed antennae, inlays or completed labels. Antennae are commonly printed with silver-based particle suspensions, such as those described above, which are compatible with both paper and polymer components of an absorbent article. Such antennae can provide performance to match traditional copper or aluminium antennae. An example of a commercially available printed antenna is FleX Wing produced by Precisia LLP.

Active wetness detecting means 26 may be designed to ensure long life of the battery, e.g. by pulsing the power supplied by the battery, or by using the battery only to power the memory and using a passive wetness detecting means 26 for generating an RF signal. The printed logic circuit may be used to monitor the printed sensor at given time intervals and save the result in the printed memory. Additionally, if the active wetness detecting means 26 comprises more than one printed sensor in different locations in the absorbent article 12, the logic circuit can be used to compare the signals from the sensors and gather data on the nature, extent and location of the wetness in the absorbent article 12. Particularly of interest are wetness detecting means 26 which provide a quantitative measure of the status of an absorbent article, rather than a simple on/off measure. Printed memory circuits can be used to maintain a record of the status of the absorbent article 12. Preferably, the memory does not require constant power supply.

Figure 11:
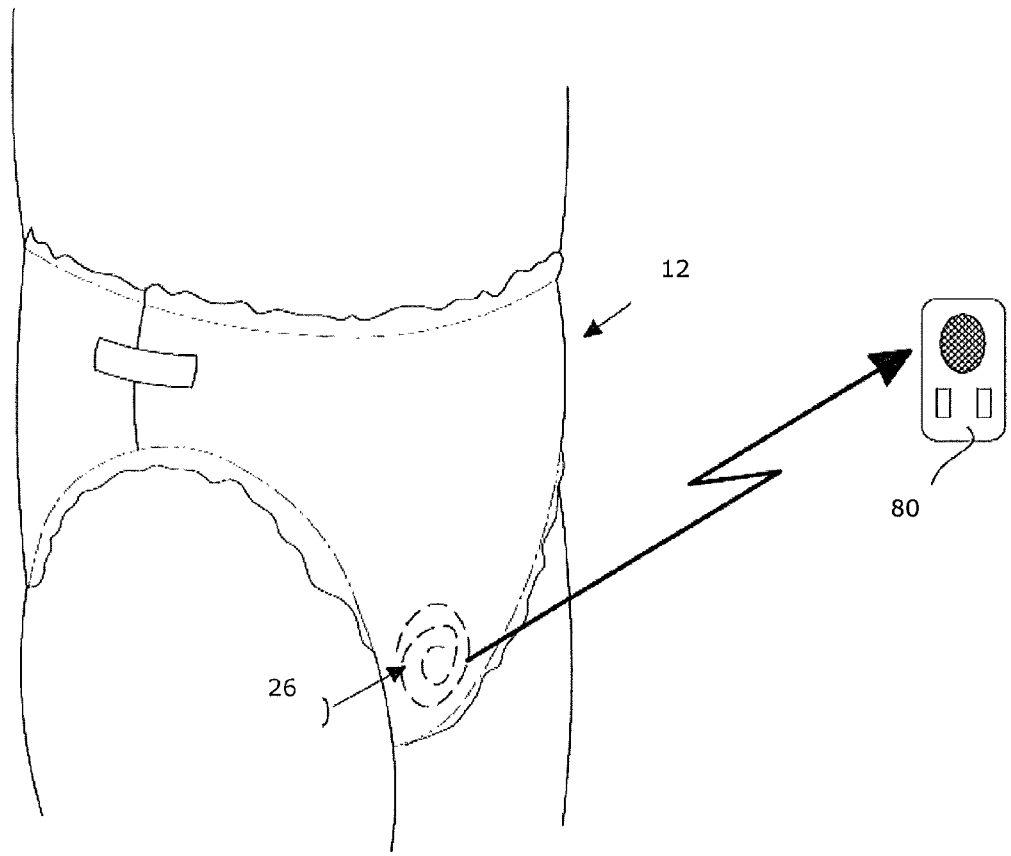
FIG. 11 shows a representation of the operation of an electrical detecting means of an absorbent article for use in a system according to an embodiment of the invention.

The absorbent article 12 is used in combination with an RF transmitter/receiver (transponder) unit 80 (FIG. 11). The transponder unit 80 comprises an inductor coil which generates an RF field and an antenna which detects an RF signal generated by an electrical circuit 44. The transponder unit 80 also comprises indicating means, such as a loudspeaker which generates an audible signal or an LED which lights up when an absorbent article 12 needs to be changed, to indicate to a caregiver that an absorbent article needs to be changed and a display screen that shows the name of the user whose absorbent article needs to be changed. The transponder unit 80 also comprises a power source (e.g. batteries) and circuitry for controlling the inductor coil, the antenna and the indicating means. The transponder unit 28 is preferably a portable handheld device.

The transponder unit 80 generates an RF field which corresponds to the resonant frequency of the electrical circuit 44. The electrical circuit 44 resonates, and the RF signal thus produced can be detected by the transponder unit 80. The RF signal generated by the electrical circuit 44 is optionally beneficially in the region 10-100 kHz. In order to be able to detect even weak RF signals generated by the electrical circuit 44, it is advantageous that the RF field generated by the transponder unit is pulsed, so that any weak RF signals generated by the electrical circuit 44 are not obscured by the RF field generated by the transponder unit 80. The electrical circuit 44 will continue to resonate for a short while after the RF field generated by the transponder unit 80 is interrupted, so that weak RF signals can be detected at the transponder unit 80. It may be advantageous for the transponder unit 80 to include a threshold, below which an RF signal generated by the electrical circuit 44 will not activate the indicating means. This will provide advantages in that an absorbent article 12 need not be changed after every soiling event, but rather the caregiver can wait until a certain level of wetness has been reached.

The transponder unit 80 may be arranged so as to scan a range of frequencies. In this way, small deviations in the resonant frequency of the electrical circuit 44 can be accommodated. Additionally, by scanning a range of frequencies, the progression of an electrical circuit 44 from an initial resonant frequency to a final resonant frequency can be seen, which also allows the caregiver to wait until a certain level of wetness has been reached before changing the absorbent article.

Optionally, the transponder unit 80 comprises a data storage unit 32, in which data concerning the number of times an absorbent article 12 is changed can be stored. This information can be downloaded to a computer and then used by caregivers to determine statistics or to make predictions for future consumption of absorbent articles. Furthermore, if a particular electrical circuit 44 provides a particular resonant frequency which can be correlated with a particular user, user-specific data can be gathered.

The wetness detecting means 26 may comprise a plurality of sensors 70 located in mutually different regions of the absorbent article 12. In this way, the nature, extent and location of the wetness in the absorbent article 12 can be monitored. It is preferred that the sensors 70 are located in the crotch region of the absorbent article 12, where wetness is most likely to be detected. Additionally or alternatively, the absorbent article 12 may comprise a plurality of wetness detecting means 26 located in mutually different regions of the absorbent article 12. If the wetness detecting means 26 is of the "short-circuit" type (as shown and described in FIG. 7*a* & *b*), it is preferably located in the crotch region of the absorbent article, where wetness is most likely to be detected. If, however, the wetness detecting means 26 is not of this type (e.g. if it is moisture-sensitive) it is advantageous for it not to be located in the crotch region, so that it is not saturated immediately upon soiling of the absorbent article 12.

Further modifications of the invention within the scope of the claims would be apparent to a skilled person.

The invention claimed is:

1. A system for associating an absorbent article with at least one of the identity and the location of a user of said absorbent article, comprising:
   an absorbent article,
   machine-readable information concerning at least one of the identity and the location of a user of the absorbent article, wherein
   the system comprises machine-readable information identifying the absorbent article,
   a reader to read the information identifying the absorbent article and the information concerning at least one of the identity and the location of the user of the absorbent article,
   a memory that is arranged to store the information identifying the absorbent article and the information concerning at least one of the identity and the location of the user of the absorbent article in a form such that on retrieval of information from the memory, the information concerning the absorbent article is automatically associated with the information concerning at least one of the identity and location of the user of the absorbent article;
   wherein the system comprises means for associating the status indication from the machine-readable sensor with the information concerning at least one of the identity and the location of the user of the absorbent article or the information identifying the absorbent article; and
   a processor arranged to notify a caregiver of a status of the absorbent article including the at least one of the identity and location of the user of the absorbent article.

2. The system according to claim 1, wherein the absorbent article comprises a machine-readable sensor that is arranged to determine and indicate the status of at least a region of the absorbent article.

3. The system according to claim 2, wherein the sensor is arranged to communicate via radio frequency communication.

4. The system according to claim 2, wherein the sensor is integrally formed with the absorbent article.

5. The system according to claim 2, wherein said sensor is a wetness detecting sensor.

6. The system according to claim 2, comprising means for indicating that the status of the absorbent article has changed.

7. The system according to claim 1, wherein the information concerning at least one of the identity and the location of the user is arranged to be located in the vicinity of the user of said absorbent article or to be attached to the user of said absorbent article, independently of said absorbent article.

8. The system according to claim 7, wherein the information concerning the identity or location of the user is arranged by means of a wristband.

9. The system according to claim 1, wherein the information concerning at least one of the identity and the location of the user is contained in an optically readable code.

10. The system according to claim 9, wherein the optically readable code is a bar code, a Radio Frequency Identification (RFID) tag, a magnetic strip, optical characters or a smart card.

11. The system according to claim 1, wherein the information concerning the identification of the absorbent article is contained in an optically readable code.

12. The system according to claim 11, wherein the optically readable code is a bar code, a Radio Frequency Identification (RFID) tag, a magnetic strip, optical characters or a smart card.

13. The system according to claim 1, wherein the system comprises data storage means arranged to record data concerning the user of said absorbent article.

14. The system according to claim 1, comprising a plurality of said absorbent articles.

15. A method for associating information identifying an absorbent article with information concerning at least one of the identity and the location of a user of said absorbent article, comprising the steps of:
   a) obtaining information identifying the absorbent article,
   b) obtaining information concerning at least one of the identification and the location of a user of the absorbent article, and
   c) storing said information identifying the absorbent article and said information concerning at least one of the identification and the location of the user of the absorbent article in a memory in a form such that on retrieval of information from the memory, the information concerning the absorbent article is automatically associated with the information concerning at least one of the identity and the location of the user of the absorbent article;
   providing the absorbent article with a machine-readable sensor that is arranged to determine and indicate the status of at least a region of the absorbent article and associating the status indication from the machine-readable sensor with the information concerning at least one of the identity and the location of the user of the absorbent article or the information identifying the absorbent article; and notifying a caregiver of a status of the absorbent article including the at least one of the identity and location of the user of the absorbent article.

16. The method according to claim 15, wherein steps a) and b) of the method are carried out when the absorbent article is put on the user.

17. The method according to claim 15, wherein the sensor is arranged to communicate via radio frequency communication.

18. The method according to claim 15, wherein the sensor is integrally formed with the absorbent article.

19. The method according to claim 15, wherein the sensor is a wetness detecting sensor.

20. The method according to claim 15, comprising a step of indicating that the status of the absorbent article has changed.

21. The method according to claim 15, comprising a step of locating the information concerning at least one of the identity and the location of the user in the vicinity of the user of said absorbent article or attaching said information to the user of said absorbent article, independently of said absorbent article.

22. The method according to claim 21, wherein the information concerning at least one of the identity and location of the user is arranged by means of a wristband.

23. The method according to claim 15, wherein the information concerning at least one of the identity and the location of a user is contained in an optically readable code.

24. The method according to claim 23, wherein the optically readable code is a bar code, a Radio Frequency Identification (RFID) tag, a magnetic strip, optical characters or a smart card.

25. The method according to claim 15, wherein the information concerning the identification of the absorbent article is contained in an optically readable code.

26. The method according to claim 25, wherein the information concerning the at least one of identity and location of the user is arranged by means of a wristband.

27. The method according to claim 15, comprising a step of recording data concerning the user of the absorbent article.

28. The method according to claim 15, comprising a step of associating information identifying a plurality of absorbent articles with information concerning at least one of the identity and the location of users of said plurality of absorbent articles.

29. A non-transitory computer program product, comprising a computer program containing computer program code means arranged to cause a computer or a processor to execute the steps of the method according to claim 15, stored on a computer-readable medium.

* * * * *